(12) United States Patent
Bruand et al.

(10) Patent No.: US 11,495,325 B2
(45) Date of Patent: Nov. 8, 2022

(54) SYSTEMS AND METHODS FOR MULTIPLEX PCR PRIMER SELECTION

(71) Applicant: Illumina, Inc., San Diego, CA (US)

(72) Inventors: Jocelyne Bruand, San Diego, CA (US); Johann Felix Wilhelm Schlesinger, San Diego, CA (US); Ryan Matthew Kelley, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 1153 days.

(21) Appl. No.: 16/035,470

(22) Filed: Jul. 13, 2018

(65) Prior Publication Data

US 2020/0017994 A1 Jan. 16, 2020

(51) Int. Cl.
*G01N 33/48* (2006.01)
*G01N 33/50* (2006.01)
*G16B 35/00* (2019.01)
*G16C 20/60* (2019.01)

(52) U.S. Cl.
CPC ............. *G16B 35/00* (2019.02); *G16C 20/60* (2019.02)

(58) Field of Classification Search
CPC ................................ G16B 35/00; G16C 20/60
See application file for complete search history.

(56) References Cited

U.S. PATENT DOCUMENTS

| 6,138,077 A * | 10/2000 | Brenner | C12Q 1/6837 |
| | | | 536/25.4 |
| 2009/0123935 A1* | 5/2009 | Jahan | C12Q 1/6851 |
| | | | 435/6.1 |

| 2016/0369333 A1 | 12/2016 | Babiarz et al. |
| 2017/0342477 A1 | 11/2017 | Jensen et al. |

FOREIGN PATENT DOCUMENTS

| EP | 2966180 A1 | 8/2017 |
| WO | 2016/172126 A2 | 10/2016 |
| WO | 2018/061695 A1 | 4/2018 |

OTHER PUBLICATIONS

Ozturk, A., et al., "A multiplex primer design algorithm for target amplification of continuous genomic regions", BMC Bioinformatics 18:306; DOI 10.1186/s12859-017-1716-7, Jun. 19, 2017, 1-9.
PCT/US2019/033602 , "International Search Report and Written Opinon", dated Sep. 5, 2019, 1-20.
Shen , et al., "MPprimer: a program for reliable multiplex PCR primer design", BMC Bioinformatics 3010 11:143, DOI: 10.1186/1471-2105-11-143,, Mar. 18, 2019.

* cited by examiner

*Primary Examiner* — Russell S Negin

(74) *Attorney, Agent, or Firm* — Knobbe Martens Olson & Bear, LLP

(57) ABSTRACT

Disclosed herein are systems and methods for multiplex primer design and selection. In one example, a system includes non-transitory memory configured to store executable instructions; and a hardware processor programmed by the executable instructions to receive a plurality of target gene sequences and determine a set of primers for each target gene sequence based on a penalty score associated with the set of primers, wherein the penalty score is based on a non-linear combination of a primer-level penalty score and a set-level penalty score.

37 Claims, 10 Drawing Sheets

Specification includes a Sequence Listing.

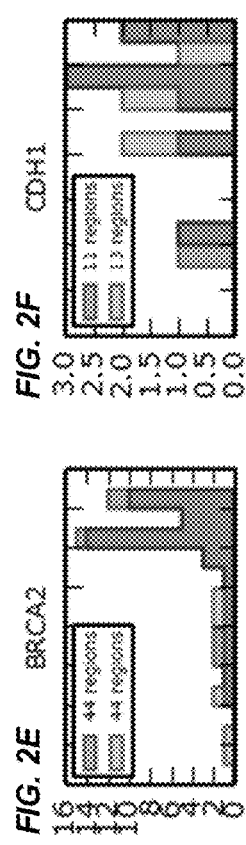
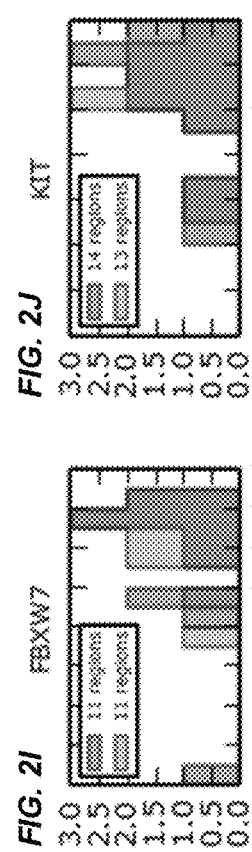
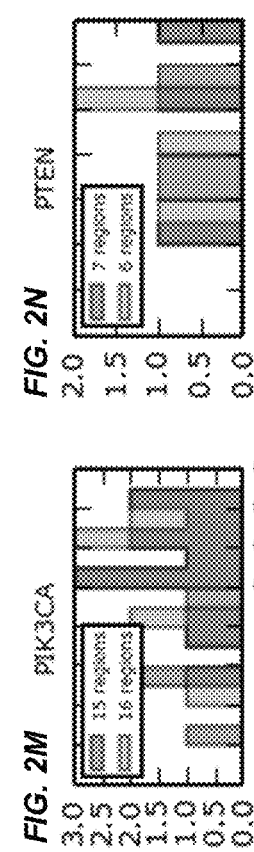
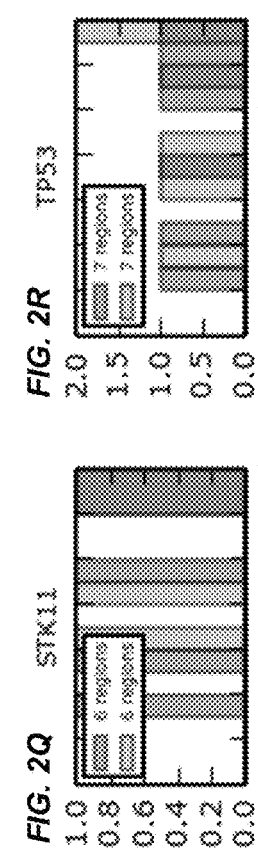

SEQ ID NO. 1  seq1: TCCTCATGTATTGGTCTCTCATGG
SEQ ID NO. 2  seq2: AGAGCATGAGAGGCCATAG

```
seq1:   5' TCCTCATGTATTGGTCTCTCATGG 3'
                   xxx||x|||||||x
seq2:            3' GATACCGGAGAGTACGAGA 5' or seq1:   5' TCCTCATGTATTGGTCTCTCATGG 3'
                   xxx||x|||||||x
```
SEQ ID NO. 3  seq2_rc:      5' CTATGGCCTCTCATGCTCT 3'

FIG. 3A

SEQ ID NO. 4  seq1:    5' TCTGAACTGCAGCATTTACTGC 3'
                             xxx|||||||||||xx|xx
SEQ ID NO. 5  seq2_rc: 5' TTTCTGCAGCATTTCTTTTCCATTG 3'

| seq1 | T | C | T | G | A | A | C | T | G | C | A | G | C | A | T | T | T | A | C | T | G | C |   |   |   |
|------|---|---|---|---|---|---|---|---|---|---|---|---|---|---|---|---|---|---|---|---|---|---|---|---|---|
| seq2_rc |   |   |   | T | T | T | C | T | G | C | A | G | C | A | T | T | T | C | T | T | T | T | C | A | T | G |
| score accum. |   |   |   | -1 | -2 | -3 | -2 | -1 | 0 | 1 | 2 | 3 | 4 | 5 | 6 | 7 | 8 | 7 | 6 | 7 | 6 | 5 |   |   |   |

FIG. 3B

SYSTEMS AND METHODS FOR MULTIPLEX PCR PRIMER SELECTION

REFERENCE TO SEQUENCE LISTING

The present application is being filed along with a Sequence Listing in electronic format. The Sequence Listing is provided as a file entitled Sequence_Listing_ILLINC_417A, created on Mar. 7, 2018, which is 1,282 bytes in size. The information in the electronic format of the Sequence Listing is incorporated herein by reference in its entirety.

BACKGROUND

Field

The present disclosure relates generally to the field of polymerase chain reaction (PCR) primer design and more particularly to designing PCR primers in silico.

Description of the Related Art

To increase assay throughput and allow more efficient use of nucleic acid samples, simultaneous amplification of many target nucleic acids in a sample of interest can be carried out by combining many oligonucleotide primers with the sample and then subjecting the sample to polymerase chain reaction (PCR) conditions in a process known as multiplex PCR. Use of multiplex PCR can significantly simplify experimental procedures and shorten the time required for nucleic acid analysis and detection. However, when multiple pairs are added to the same PCR reaction, non-target amplification products may be generated, such as amplified primer dimers. The risk of generating such products increases as the number of primers increases. These non-target amplicons significantly limit the use of the amplified products for further analysis and/or assays. Thus, there is a need for primer design and selection that enables efficient and successful multiplex PCR.

SUMMARY

Disclosed herein are systems and methods for amplifying sub-target regions of target gene sequences. In one example, a system includes non-transitory memory configured to store executable instructions; and a hardware processor programmed by the executable instructions to perform a method comprising: receiving a plurality of target gene sequences; determining a designability score of each target gene sequence; splitting each target gene sequence into a plurality of sub-target regions based on the determined designability score; assigning each sub-target region to a first pool or a second pool of sub-target regions; determining a set of primers for each sub-target region in each pool and a penalty score associated with the set of primers based on a non-linear combination of properties of primers in the set of primers and an amplicon amplifiable from the sub-target region using the set of primers.

Another embodiment is a computer-implemented method that includes receiving a plurality of target gene sequences; determining a designability score of each target gene sequence; splitting each target gene sequence into a plurality of sub-target regions based on the determined designability score; assigning each sub-target region to a pool of one or more pools of sub-target regions; for each pool of the one or more pools: computing a penalty score for each set of sets of candidate primers per sub-target region based on a non-linear combination of properties of candidate primers in the set of candidate primers and an amplicon amplifiable from the sub-target region using the set of candidate primers; computing a primer pool score between sets of candidate primers across sub-target regions within the pool; selecting a set of primers from the sets of candidate primers for each sub-target region in the pool based on the computed penalty scores. The penalty score for each set of candidate primers can include a primer-level penalty score and a set-level penalty score. The primer-level penalty score and the set-level penalty score may be updated heuristically. The penalty score may include a pool-level penalty score that is computed for each probe set. The pool-level penalty score may indicate the effect of one probe set, or each probe set, in a pool on other probe sets in the pool.

Another example is a computer-implemented method that includes receiving a plurality of target gene sequences; and determining a set of primers for each target gene sequence based on a penalty score associated with the set of primers, wherein the penalty score is based on a non-linear combination of a primer-level penalty score and a set-level penalty score.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIGS. 3A and 3B depict exemplary processes of determining overlap scores for primer selection.

DETAILED DESCRIPTION

Figure 1A:
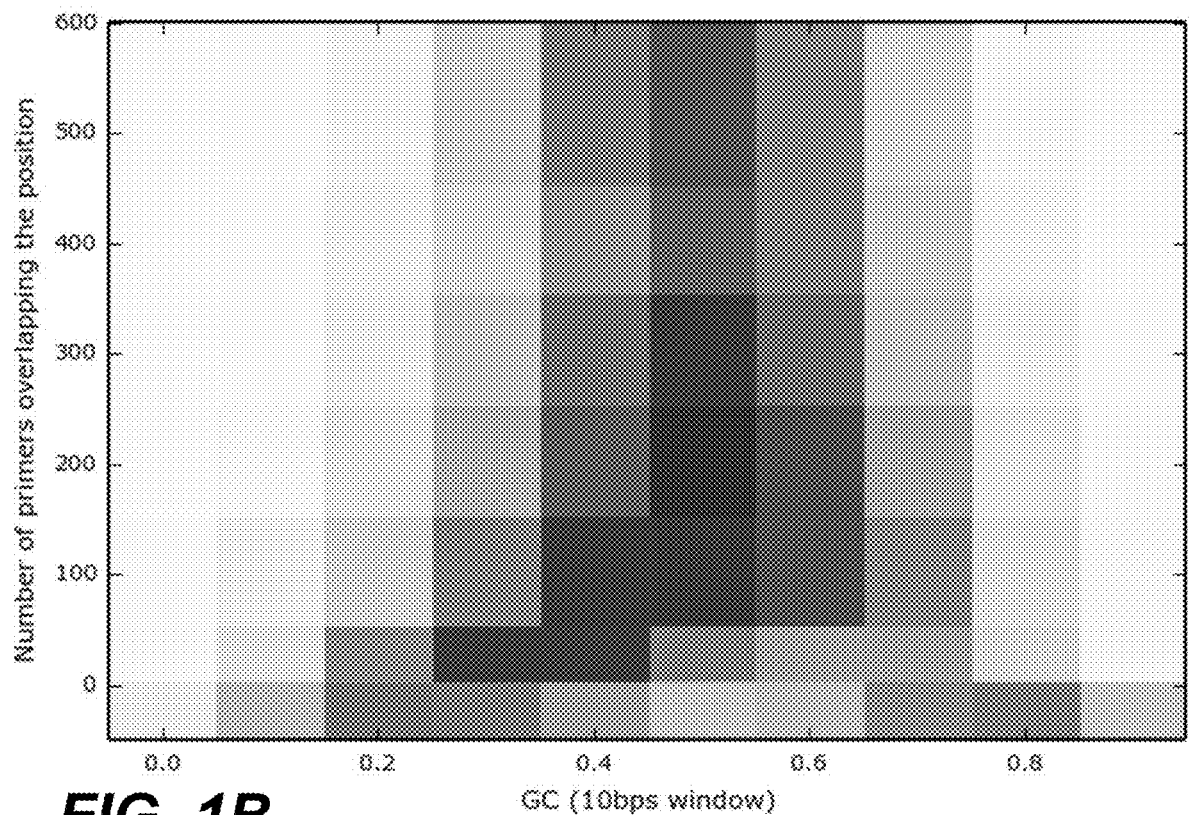
FIGS. 1A and 1B are exemplary plots illustrating that the GC content of a target gene sequence can be used as a measure of the designability of the target gene sequence.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Overview

One embodiment is a system and method for selecting a set or a pool of primers for multiplex PCR of target gene sequences of interest. The set of primers selected can be sued for amplifying sub-target regions of target gene sequences. In one example, a designability score for each target sequence is first determined. This is explained more fully below, but the designability score relates to the effectiveness of designed primers to efficiently amplify the target gene sequence. Designability may be determined based on the number of candidate primers in the target gene sequence, the quality of candidate primers in the target gene sequence, and scoring across multiple features of the target gene sequence. After determining a designability score of each target gene sequence, each target gene sequence may be split into a plurality of sub-target regions based on the determined designability score, and each sub-target region can be assigned to a first pool or a second pool of sub-target regions. Subsequently, a set of primers can be selected or determined for each sub-target region in each pool and a penalty score associated with the set of primers based on a non-linear combination of properties of primers in the set of primers and an amplicon amplifiable from the sub-target region using the set of primers In one implementation, a set of primers can be designed and selected using a penalty score based on a non-linear combination of a primer-level penalty score and a set-level penalty score. For example, a set of primers can be designed and selected in silico using thermodynamic properties of primers, dimer formation properties or predictions, intended target specificity, or a combination thereof. Thermodynamic properties and dimer formation properties of primer may be used to determine a primer-level penalty score. Intended target specificity may be used to determine a set-level penalty score.

Designability

Disclosed herein are systems and methods for designing and selecting primers for amplifying sub-target regions of target gene sequences for multiplex PCR. In one embodiment, a method can include determining a designability score of each target gene sequence. In order to design primers to tile a large region of one or more target gene sequences, each target gene sequence can be split into multiple subpools, such as two subpools. Instead of splitting randomly, the splitting may be based on estimated designability across the region. The splitting may be done to optimize the chances of subsequent primer selection. Designability of a target gene sequence can be assessed in several ways. For example, the designability can be determined based on the number of candidate primers in the target gene sequence, the quality of candidate primers in the target gene sequence, and scoring across multiple features of the target gene sequence. Such features include GC content of the target gene sequence, presence and the number of known variants in the target gene sequence, presence and the number and length of poly-N stretches in the target gene sequence.

Figure 1B:
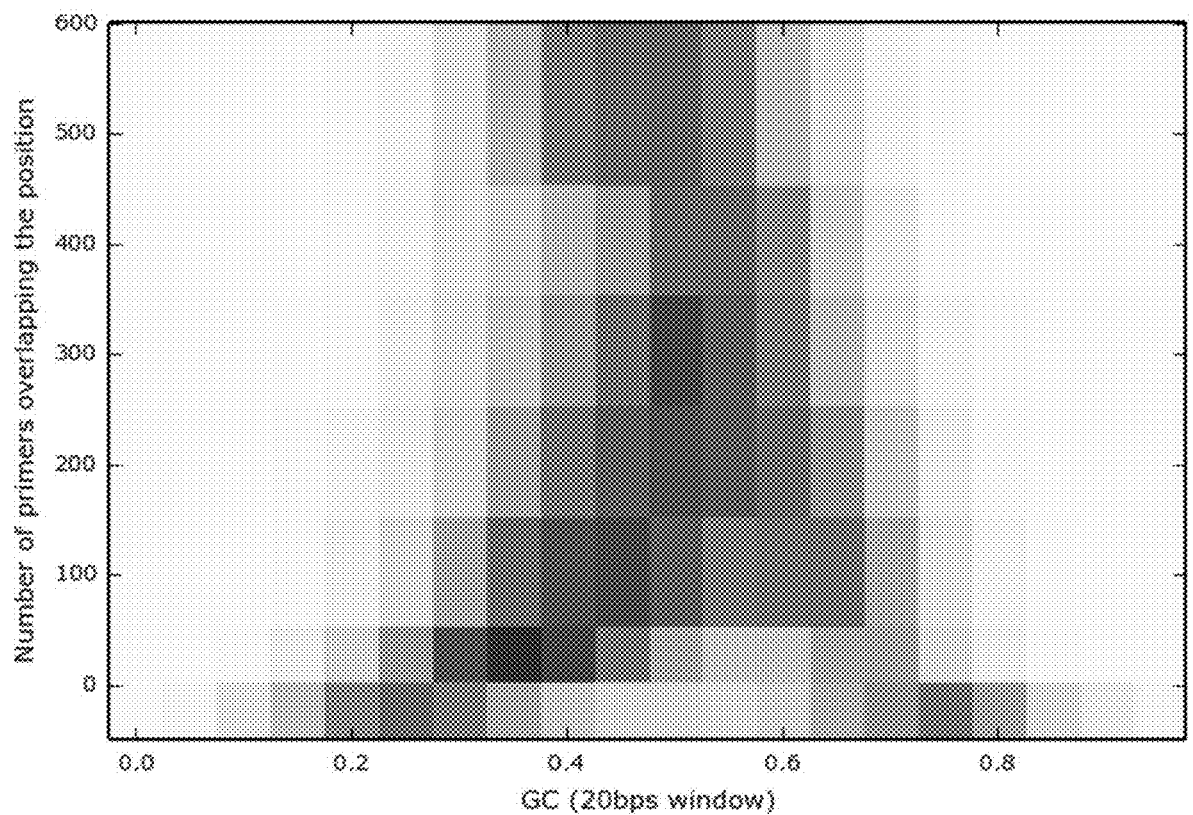

Criteria for designability. FIGS. 1A and 1B are exemplary heat maps illustrating that the GC content of a target gene sequence can be used as a measure of the designability of the target gene sequence. In FIGS. 1A and 1B, darker regions indicate higher designability, as indicated by the number of candidate primers overlapping a particular position in the target gene sequence. For a 20-base pair window, designability may be higher for GC content between 0.35 and 0.65. In one embodiment, criteria for estimating designability can be based on preferred GC content range of 0.35-0.65, fewer number or lack of poly-N stretches of six or more base pairs, and fewer number or lack of single nucleotide polymorphisms (SNPs). SNP information may be obtained from a NP database (dbSNP) and Catalogue of Somatic Mutations in Cancer (cosmic). In one embodiment, primers may be first designed across the entire large region to tile. Bad primers may be filtered out based on designability or other design criteria. Subsequent splitting may be based on the actual number of passing primers.

Bad regions. In one implementation, a nucleotide position of the target gene sequence can have low designability or is considered as bad if it is part of a poly-N stretch of six or more base pairs, the GC for the 20 bps window around it being less than 0.35 or more than 0.65, there are more than two SNPs from dbSNP in the 20 bps window around it, and/or there are more than two cosmic mutation above a cosmic threshold in the 20 bps window around it. The cosmic threshold may be set to mean plus one or more standard deviations computed across positions across one or more exons. To avoid tiny blocks, a region with higher designability or a good regions with at most 10 base pairs (i.e., half the window for calculating GC content) may be merged into neighboring bad regions. Alternatively, or additionally, bad regions with at most 10 bps may be merged into neighboring good regions. In one embodiment, a goodness or badness metrics may be computed.

Target Splitting/Tiling

Based on the designability score, each target gene sequence can be split into a plurality of sub-target regions. Given a set of hard-to-design sub-target regions of a region, primers for the region can be designed in a divide and conquer method. In one embodiment, splitting can be done in a divide-and-conquer manner recursively.

For example, after a split point is determined and a target gene sequence is split into two sub-target regions, a split point may be determined in each sub-region. In one embodiment, all the good blocks can be split. A split point should be legal, such as no more than a maximum length away from either end of a block containing the split point. If a split point allows at least a certain number of base pairs, such as 30, on each side of the split point in the block, it may be preferred as it may allow enough room for probe design. A preferred split point may be selected over a non-preferred split point. If there are multiple preferred split points within a block, the preferred split point closest to the mid-point of the block may be selected. In order to avoid odd edge effects from previous splitting, after recursion the two newly adjacent sub-target regions may be re-split, or merged. A merging criterion may be total length of the two newly adjacent sub-target regions. In one implementation, a split point in a target gene sequence, or a sub-target region, may be determined by finding a window in the sequence with the most badness, and then using the largest good block in the window with the most badness.

As another example, a split point in a target gene sequence, or a sub-target region, may be considered legal if the resulting sub-target regions on each side of the split point are either on the edge of the target gene sequence, or can be split legally. There may exist a legal split if and only if any one of equivalent, or approximately equivalent conditions expressed in Equations [1]-[4] is satisfied.

$$\exists n \in \mathbb{N}^+: n*t_{min} \leq l \leq n*t_{max} \qquad \text{Equation [1]}$$

$$\exists n \in \mathbb{N}^+: \frac{l}{t_{minx}} \geq n \wedge \frac{l}{t_{max}} \leq n \qquad \text{Equation [2]}$$

$$\exists n \in \mathbb{N}^+: \frac{l}{t_{max}} \leq n \leq \frac{l}{t_{min}} \qquad \text{Equation [3]}$$

$$\left\lceil \frac{l}{t_{max}} \right\rceil \leq \left\lfloor \frac{l}{t_{min}} \right\rfloor \qquad \text{Equation [4]}$$

A split window may be selected using a moving average of the badness score and a badness score vector. In one embodiment, the preferred split in order of priority is (1) enough goodness on both sides of a split point, (2) the largest good block in terms of effective length, (3) the split being closest to the middle of a window of a target gene sequence, and (4) the split being closest to the middle of a block. A block length may be computed with plus/minus the minimum length for a preferred split. The effective length may be determined such that the mid-point of a block is within a window.

Pool Assignment

After splitting a target gene sequence into a plurality of sub-target regions, each sub-target region can be assigned to one of two or more pools of sub-target regions. Assignment may be done by balancing by target gene sequences and by lengths such that each target gene sequence has similar numbers of amplicons in each pool, and the pools have similar distributions of lengths of sub-target regions.

Balancing lengths. Assigning sub-target regions into pools may include balancing lengths of sub-target regions in each pool using binned count vectors of lengths. Lengths of sub-target regions may be counted in bins of x base pairs. For example, if the bins are 10 base pairs and the lengths are 115, 119, and 30 base pairs for a pool, then there are two regions in the bin of 110-119 base pairs and one region in the bin of 30-39 base pairs. The pseudocodes below illustrate an exemplary process of assigning sub-target regions into two pools.

Initiate binned counts vectors c1 and c2 corresponding to the two pools to zeros across.

From the target gene sequence with most number of sub-target regions to the target gene sequence with least number of sub-target regions:

Split the sub-target regions into two sub-target pools, sub-target pool 1 and sub-target pool 2, as 1, 2, 1, 2, etc.

Get the corresponding binned counts of the region lengths in each pool: v1 and v2

Compute the distance between the two assignment possibilities.

d1=distance(c1+v1, c2+v2)
d2=distance(c1+v2, c2+v1)

If d1<d2, assign target pool 1 to pool 1 and target pool 2 to pool 2, else if d1>d2, assign sub-target pool 2 to pool 1 and sub-target pool 1 to pool 2, else (tie on distribution), assign to even out number of targets in pools.

The distance measure may be a city block distance, such as the Manhattan distance, the L1 norm $\|u-v\|_1$ or a higher order norm.

Handling genes. If two target gene sequences are two exons which are less than a threshold length apart from each other in a genome, the adjacent sub-target regions of these exons may be assigned to different pools. Then the target pool 1 and target pool 2 in the above pseudocodes may be referred to as gene pool 1 and gene pool 2.

Combining genes into pools. The genes pools may then be combined to also balance the lengths of sub-target regions in the final pools. For example, for each gene, whether gene pool 1 is assigned to pool 1 and gene pool 2 is assigned to pool 2, and vice versa, has to be determined.

Figure 2B:
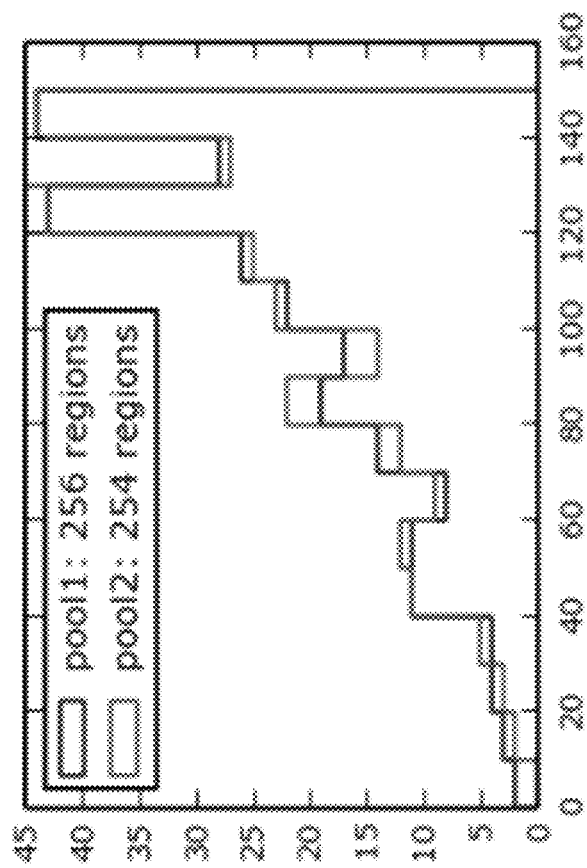
FIGS. 2A-2R are exemplary plots showing results of assigning a plurality sub-target regions of target gene sequences into a pools for multiplex PCR primer selection.
Figure 2A:
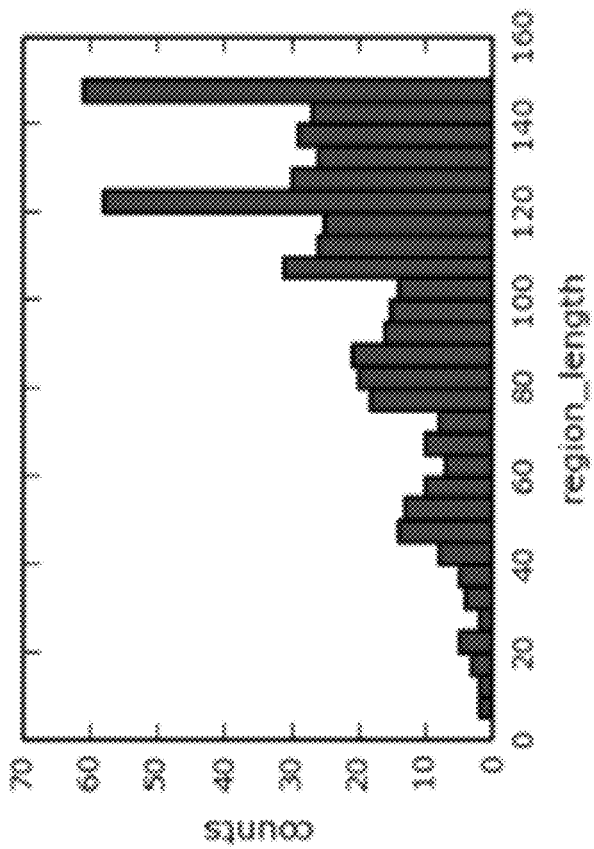

FIGS. 2A-2R are exemplary plots showing results of assigning a plurality sub-target regions of target gene sequences into a pools for multiplex PCR primer selection. The sub-target regions of the 16 genes shown in FIGS. 2C-2R are split into two pools. FIGS. 2C-2R are plots showing even distributions of these 16 genes in the two pools. FIG. 2B is a plot showing the overall even distribution of these 16 genes in the two pools. The overall length distribution of the sub-target regions of these 16 genes are shown in FIG. 2A Primer Selection After assigning the sub-target regions to the two pools, a set of primers for each sub-target region in each pool, and a penalty score associated with the set of primers, can be determined. The penalty score may be determined based on a non-linear combination of a primer-level penalty score and a set-level penalty score. The primer-level penalty score may include thermodynamics penalty of primers in the set of primers, an adapter binding penalty, a known variant penalty, or a combination thereof. The set-level penalty score may include a PCR amplicon penalty, an off-target penalty, an intra-set primer interaction penalty, or any combination thereof. The off-target penalty may be based on one or both of the off-target length and the intended target length. The penalty score may be determined using a pool level penalty based on interlocus off-targets and interactions between primers for different target gene sequences. Scores may be computed and stored at different levels to improve run time. A set can be: a single primer, a pair of primers, or a set of three primers. A set of three primers may include a pair of primers and an internal probe (or primer).

There may be a specificity check score. Specificity checking may be done against a different target gene sequences. For example, specificity checking can be done against a reference, such as the whole human genome when designing multiplex primers for a human panel of target gene sequences. Other references include transcriptome with genome (for RNA design) and multiple bacterial genomes (for bacterial design).

General Scoring. Many of the feature scoring functions are bounded in which no penalty occurs below (or above) a certain value, and an extremely high penalty occurs above (or below) another value. In between the bounds, the scoring function may assume any mathematical function, such as linear, polynomial, etc. Some scoring functions may be based on multiple features.

Probe Thermodynamics Scoring. Some features may be normalized by their allowable range, such as primer melting temperature (primerTm), primer length (primerLen), and primer GC content (primerGC). Equation [5] may be used to normalize a penalty associated with a primer's melting temperature (primerTm_penalty).

$$\text{primerTm\_penalty} = \text{primerTm}/(\text{max\_primerTm} - \text{min\_primerTm}) \qquad \text{Equation [5]}$$

The overall thermodynamic penalty (primerTherm_penalty) may be computed as shown in Equation [6] below.

$$\text{primerTm\_penalty}=2*\text{primerTm\_penalty}+\text{primerLen\_penalty}+\text{primerGC\_penalty} \quad \text{Equation [6]}$$

The resulting penalty may be bounded and scaled or normalized.

Fast Dimer Checking. A dimer scorer may assign a penalty for two sequences indicating how bad of a dimer they could form. Dimers may be scored differently based on the sequence type. For example, primer-adapter dimers and forward-reverse dimers may be more heavily penalized than forward-forward and reverse-reverse dimers. Bounds may be kept tighter, and the penalty higher for each overlapping base. If an internal probe or primer is used, its potential dimers may also have different scoring function, depending on how the internal probe is used.

In some embodiments, two features are used for dimer prediction: the number of 3' bases overlap and thermodynamics binding. Thermodynamics binding may be determined only in the final iterations of the method to minimize computation time. In one example, the number of 3' base overlap may be determined by, for each possible 3' overlap between two sequences, counting the number matches and subtracting from the matches counted the number of mismatches for the best semi-global alignment. The overlap with the highest score may be retained.

As another example, given sequences seq1 and seq2, and given a specific amount of overlapping bases on their 3' end, the number of matches minus the number of mismatches for the best semi-global alignment may be computed. The alignment should go all the way to one of the 3' sequence (but not necessarily both). This may be computed by going from the 3' end and scoring 1 for a match and −1 for a mismatch. The final score is the maximum score over all possible overlaps. FIG. 3A depicts one example of determining overlap scores for primer selection. The best overlap in the example is 13 base pairs. The score is computed from the 3' end of seq2, yielding to 11 matches and 2 mismatches, so the score is 11−2=9. In FIG. 3A, seq2_rc denotes the reverse complement of seq2.

If computing the score from the 3' end results in too many mismatches, it is possible to terminate the computation early and retain the best score so far. FIG. 3B depicts one such example. FIG. 3B shows the result if the score coming from the seq4_rc is accumulated. If computation stops as soon as the score dropped below t=0, then it would not be able extend in either direction due to the mismatches on both 3' ends, which would immediately drop the score to −1. In one embodiment, a −1 threshold may be used for early termination of computation. Changing this threshold would allow the computation to jump over a set of mismatches more easily, particularly in the edge (at the cost of computation). In this example, the threshold can be set to t=−3 or less to allow for the 3 mismatches in the 3' end. If t≤−½*overlap, then the computation is guaranteed to check all possibilities that would yield to final positive score. Phrased differently, if the number of mismatches is more than half of the sequence length, there would not be enough alignment to recuperate. The match and mismatch score can be dependent on AT vs. GC base pair Amplicon Scoring. In PCR, shorter amplicons tend to amplify better than their longer counter-parts. Also, amplicons with mid-range GC contents tend to outperform amplicons with wider GC range. Furthermore, primer melting temperature (Tm) tends to be correlated to amplicon GC content, possibly due to the general GC content of the target region. However, increasing primer Tm can help with low GC amplicons. Thus, a scoring function that takes in as features amplicon GC, amplicon length and primer Tm may be used. The scoring function may be trained using linear regression, with best results achieved as shown in Equation [7].

$$\text{coverage}=\beta 1*\text{ampliconGC\_penalty}*\text{ampliconLen\_penalty}+\beta 2*\text{ampliconGC\_penalty}*\text{primerTm\_penalty}+\varepsilon \\ (DF=2), \quad \text{Equation [7]}$$

where ampliconGC_penalty=|amplicon_gc−ideal_amplicon_gc|/amplicon_GC _range, primerTm_penalty=(max _primer_tm−min(forwardTm,reverseTm))/(max_primer_tm−min_primer_tm), and ampliconLen_penalty=amplicon_length/max_amplicon_length.

Figure 4:
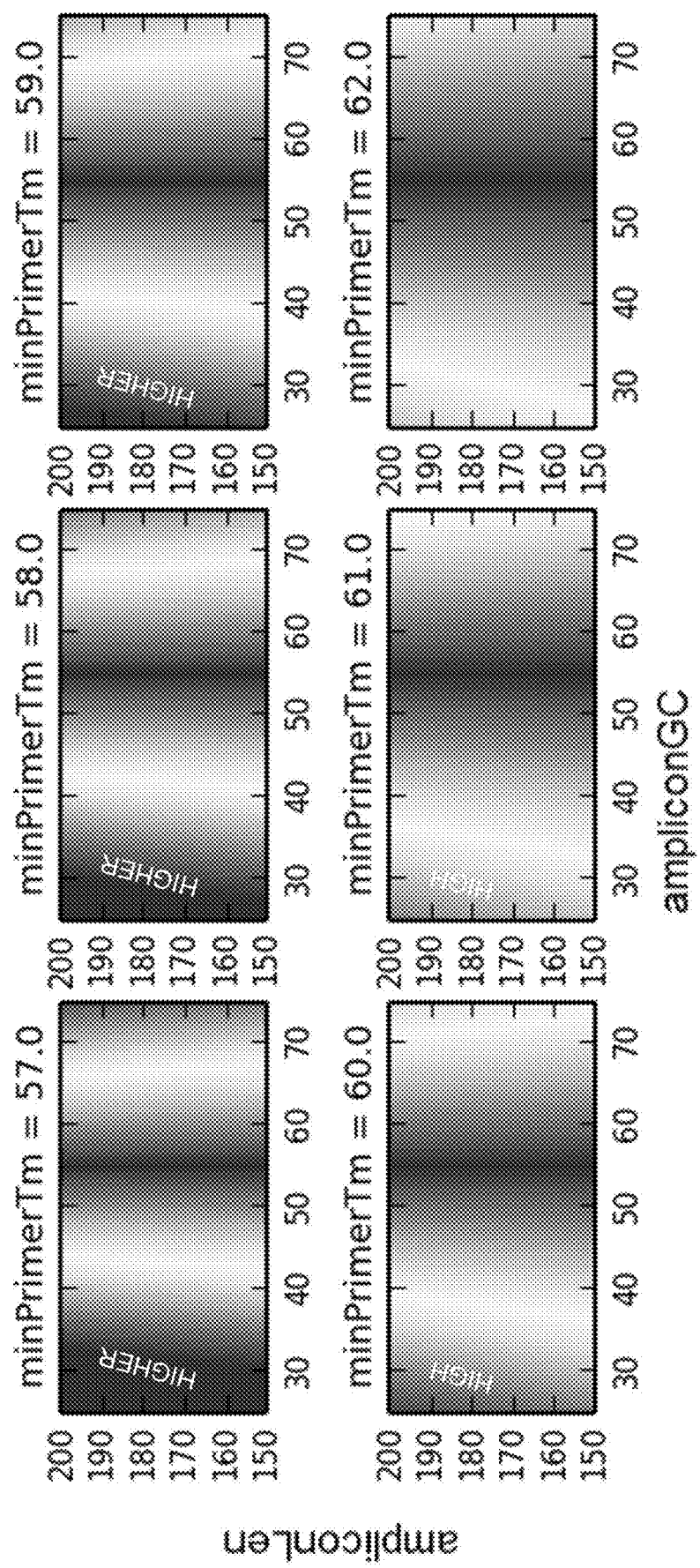
FIG. 4 shows exemplary plots of penalty scores with different amplicon lengths, amplicon GC contents, and different primer melting temperatures (Tm).

The ratio of $\beta 1:\beta 2$ may be approximately 1:1.5. FIG. 4 shows exemplary plots of penalty scores with different amplicon lengths, amplicon GC contents, and different primer melting temperatures (Tm). The figure shows that the penalty scores are higher with lower primer melting temperatures, lower amplicon lengths, and both low and high GC contents.

Multiplex selection. From the target gene sequence with the highest penalty score to the lowest penalty score, from the list of improvable target gene sequences, go through the candidate primers and pick the first candidate primer that gives a minimum desirable improvement in penalty against the rest of the pool, such as 5%. For the original set, design from the target gene sequence with fewest number candidate primers to the target gene sequence with the highest number of candidate primers. All targets are in the first set of redesignable targets. Each time the set of primers for a target gene sequence is changed, any other target gene sequence with which the interaction penalty increases becomes redesignable.

In one embodiment, if all candidate primers for a target gene sequence are compared against the current set of primers selected, the lowest penalty candidate for that target gene sequence against the current set can be determined. This can be marked as optimized, and automatically skipped for subsequent computation. However, if another pair of primers for another target gene sequence is swapped, and the new interaction penalty between this and the other pair is higher with the new pair, then the primer pair may be unmarked as optimized. Although this does not guarantee that the set of optimized primers is always truly optimized against the current set, but it is an approximate heuristic that greatly decreases computation time.

Multiplex PCR Primer Selection

Figure 5:
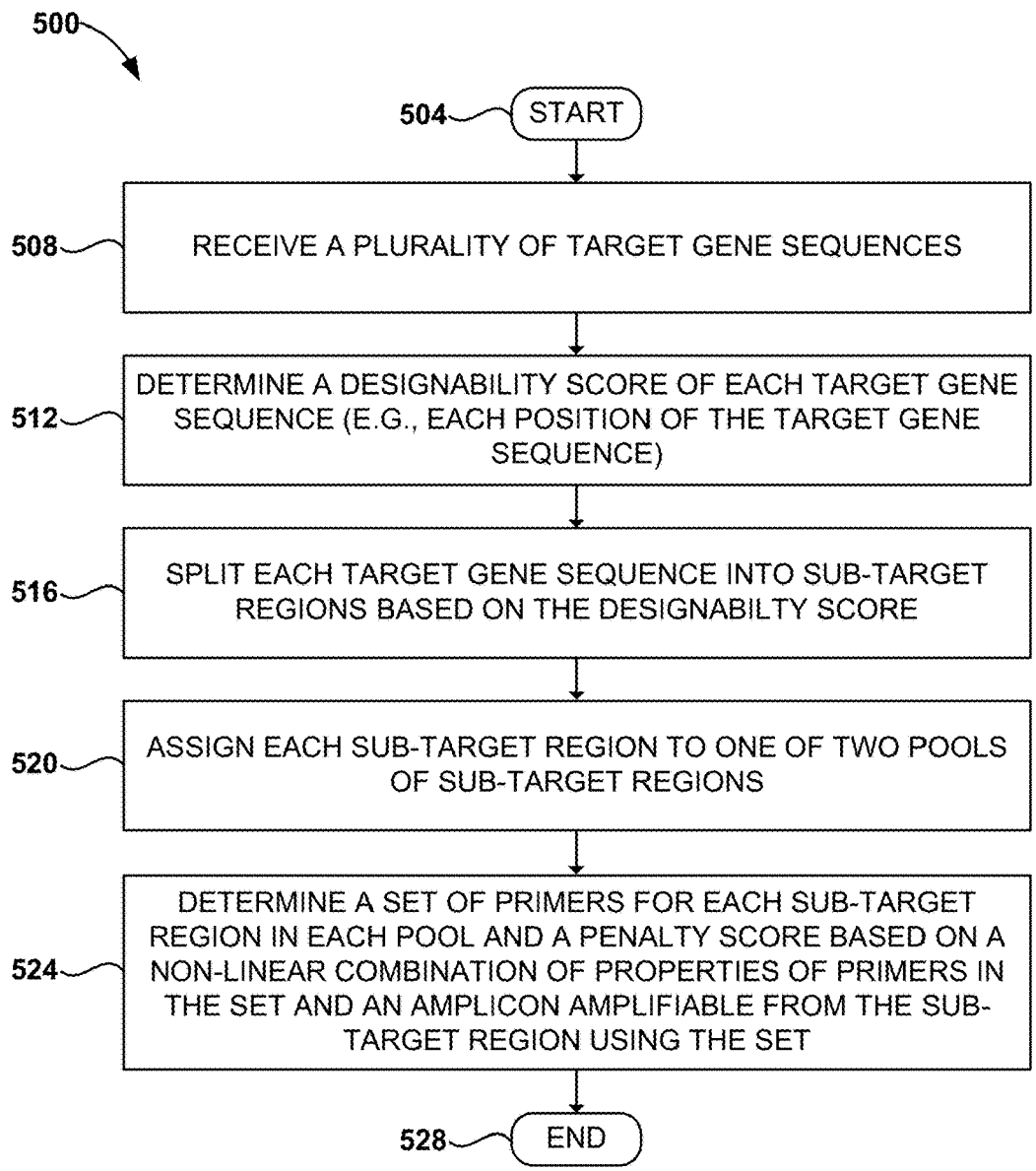
FIG. 5 is a flow diagram showing an exemplary method of selecting primers for amplifying sub-target regions of target gene sequences for multiplex PCR selection.

FIG. 5 is a flow diagram showing an exemplary method 500 of selecting primers for amplifying sub-target regions of target gene sequences for multiplex PCR. The method 500 may be embodied in a set of executable program instructions stored on a computer-readable medium, such as one or more disk drives, of a computing system. For example, the computing system 900 shown in FIG. 9 and described in greater detail below can execute a set of executable program instructions to implement the method 500. When the method 500 is initiated, the executable program instructions can be loaded into memory, such as RAM, and executed by one or more processors of the computing system 900. Although the method 500 is described with respect to the computing system 900 shown in FIG. 9, the description is illustrative only and is not intended to be limiting. In some embodiments, the method 500 or portions thereof may be performed serially or in parallel by multiple computing systems.

After the method 500 begins at block 504, the method proceeds to block 508, where a computing system receives a plurality of target gene sequences. The target gene sequences can be gene sequences of interest. The method 500 can be used to design and select primers for sequencing the target gene sequences. For example, the primers selected may be used for multiplex PCR. Use of multiplex PCR can significantly simplify experimental procedures and shorten the time required for analysis of the target gene sequences. The primers selected may enable efficient multiplex PCR with high coverage of the target gene sequences, while minimize non-target amplification products.

The method 500 proceeds from block 508 to block 512, where the computing system determines a designability score of each target gene sequence. The designability score of each target gene sequence can be different in different implementations. For example, the designability score of the target gene sequence may include a designability score of each position of the target gene sequence. As another example, the designability score of the target gene sequence may include a designability score of each sub-target region of the target gene sequence. The designability score of at least one sub-target region may be lower than a designability score threshold, which may be determined empirically. Alternatively, or additionally, the designability score of each sub-target region may be determined based on a number of candidate primers in the sub-target region, a quality score of the candidate primers in the sub-target region, a GC content of the sub-target region, presence of a poly-N stretch in the sub-target region, presence of repeats in the sub-target region, presence of a known variant in the sub-target region, or a combination thereof. The known variant may be a single nucleotide polymorphism (SNP).

After determining the designability score at block 512, the method 500 proceeds to block 516, where the computing system splits each target gene sequence into a plurality of sub-target regions based on the determined designability score. For example, the target gene sequence may be split into two sub-target regions based on a minimum allowed sub-target region length, a maximum allowed sub-target region length, a length of the target gene sequence, or a combination thereof. As another example, the target gene sequence may be split into two sub-target regions by determining a plurality of legal split points, and selecting one of the plurality of legal split points as the split point for splitting the target gene sequence based on goodness scores of the resulting split. In one embodiment, the target gene sequence may be split into more than two sub-target regions, such as three, four, five, ten or more sub-target regions.

The method proceeds from block 516 to block 520, where the computing system assigns each sub-target region to a first pool or a second pool of sub-target regions. For example, each sub-target region may be assigned to the first pool or the second pool by balancing the number of amplicons of each target gene sequence in each pool. Alternatively, or additionally, each sub-target region may be assigned to the first pool or the second pool by balancing a distribution of lengths of sub-target regions in each pool.

After assigning each sub-target region to a first pool or a second pool at block 520, the method 500 proceeds to block 524, wherein the computing system determines or selects, for each pool of sub-target regions, sets of candidate primers for each sub-target region in the pool and an associated penalty score. The penalty score may be determined based on a primer-level penalty score and a set-level penalty score. The primer-level penalty score may be based on a non-linear combination of thermodynamics penalty of primers in the set of primers, an adapter binding penalty, a known variant penalty, or a combination thereof. The set-level penalty score may include a PCR amplicon penalty, an off-target penalty, an intra- set primer interaction penalty, or any combination thereof. In one embodiment, the computing system may determine coefficients for the non-linear combination. A set of primers can include a forward primer, a reverse primer, and/or an additional primer. The additional primer may be used for enriching or cleanup of an amplicon amplifiable from a sub-target region using the forward primer and the reverse primer.

In one embodiment, to determine the set of primers for the each sub-target region in the each pool and the penalty score, the computing system may determine first sets of primers for sub-target regions of a first target gene sequence of the plurality of target gene sequences in the first pool based on a first penalty score, and then determine second sets of primers for sub-target regions of a second target gene sequence of the plurality of target gene sequences in the first pool based on a second penalty score and the first sets of primers. Subsequently, the computing system may determine updated first sets of primers for sub-target regions of the first target gene sequence based on a first updated penalty score and the second sets of primers.

In another embodiment, to determine the set of primers for each target gene sequence, the computing system may determine first sets of optimized primers for a first target gene sequence of the plurality of target gene sequences from first sets of candidate primers based on a first penalty score, and then determine second sets of optimized primers for a second target gene sequence of the plurality of target gene sequences from second sets of candidate primers based on a second penalty score and the first sets of primers. The computing system may further determine updated first sets of optimized primers for the first target gene sequence from the first sets of candidate primers based on a first updated penalty score and the second sets of optimized primers.

To determine the updated first sets of optimized primers for the first target gene sequence, the computing system may replace a first set of primers of the first sets of optimized primers with an updated first set of primers of the first sets of candidate primers to generate the updated first sets of optimized primers. The first penalty score may be based on the first set of primers, and the first updated penalty score may be based on the updated first set of primers. In one embodiment, the first penalty score is at least 5% higher than the first updated penalty score. To determine the set of primers for each target gene sequence, the computing system may determine updated second sets of optimized primers for the second target gene sequence from the second sets of candidate primers based on a second updated penalty score and the updated first sets of optimized primers. A first interaction penalty between the first set of primers and the second sets of optimized primers may be lower than an updated first interaction penalty between the updated first set of primers and the second sets of optimized primers. The number of the first sets of candidate primers may be greater or lower than the number of the second sets of candidate primers.

In one embodiment, to determine the first sets of optimized primers for the first target gene sequence, the computing system may iteratively replace a first set of primers with an updated first set of primers of the first sets of candidate primers to obtain an updated first sets of primers with a lower first penalty score. Alternatively or additionally, the computing system may iteratively replace a first set of primers with an updated first set of primers of the first sets of candidate primers to obtain the first sets of optimized primers with a lowest first penalty score.

In one embodiment, the method 500 can include designing a pool of primer sets or probe sets and redesigning and/or re-scoring one set of primers at a time. For example, the method 500 can include designing a pool of 500 sets of primers for 500 loci and redesigning and/or re-scoring a set of primers for a locus at a time. In this example, there can be 500 loci with 1000 candidate primers per set per locus. The method can include picking the worst scoring locus, and checking its candidates to see if a set of candidate primers that has a better score with the other 499 in the pool can be found. If an improvement over a threshold is achieved, this new set of candidate primers can replace the previous set of candidate primers for this locus. The method 500 can include redesigning and/or re-scoring all 500 loci one by one in that order (unless a set of candidate primers for a locus is optimized and cannot be improved).

In some embodiments, the method 500 can keep track of "optimized" and "non-optimized" primer sets. For example, if all 1000 candidates for a locus have been evaluated against the current sets of primers for the other 499 loci, the best set of candidate primers for the locus has been determined and can be marked as "optimized." In one embodiment, whether a set of primers for a locus has been changed, interactions between the set of primers in the pool for this locus with other sets of primers for the other 499 loci in the primer set changes and can be reevaluated. In one implementation, to save on compute time, a set of primers for a locus is unmarked from the optimized state if a set of primers for another locus in the pool that is changed and an interaction between the set of primers for the locus and the set of primers for the other locus is worsened than the previous interaction between the set for primers for the locus and the previous set of primers for the other locus.

The penalty score may be different in different embodiments. In one embodiments, the penalty score includes an off-target penalty of the set of primers determined based on the specificity of the set of primers for the each sub-target region in the each pool relative to a reference sequence. The reference sequence can be a whole human genome reference sequence, a transcriptome reference sequence, a bacterial genome reference sequence, a viral genome reference sequence, or a combination thereof.

In some embodiments, the method 500 can include synthesizing the sets of primers determined. The method 500 may include amplifying gene sequences of interest using the sets of primers determined. The sets of primers determined can be used for multiplex amplification of a sample, such as a genomic DNA sample. Amplified products can be amplified to determine the genotypes, predict phenotypes, and/or confirm phenotypes of the subject. The method 500 proceeds to block 532, where the method 500 ends.

Panel Designs

Sets of primers were designed and selected for multiplex PCR using a non-linear combination penalty score function of the present disclosure. The sets of primers were designed and selected to target regions with different known variants between two control samples (NA 12877 and NA 12878). Each set of primers included a forward primer and a reverse primer for PCR, and an internal primer for cleaning up products of multiplex PCR to improve specificity. The performance of the sets of primers were determined by performing multiplex PCR using the forward and reverse primers, followed by clean up using the internal primers. Table 1 shows the exemplary performance for two designs of sets of primers. For each design, multiplex PCR was repeated three times to determine the performance of the design. Specificity is the percentage of amplicons from multiplex PCR that were on target. Specificity lower than 75% may be considered as poor specificity. Specificity greater than, or equal to, 75% and lower than 80% can be considered moderate specificity. Specificity greater than, or equal to, 80% and lower than 90% can be considered good specificity. Specificity greater than 90% can be considered excellent specificity. The cutoff for acceptable specificity (LSL, lower specification limit) can be set at 80% in one embodiment, although other lower specification limits are contemplated. Uniformity is the percentage of amplicons produced by the primer sets that have coverages that are within 20% of the mean coverage of amplicons. Uniformity lower than 80% can be considered as poor uniformity. Uniformity greater than, or equal to, 80% and lower than 85% can be considered as moderate uniformity. Uniformity greater than, or equal to, 85% and lower than 95% can be considered as good uniformity. Uniformity greater than 95% can be considered as excellent uniformity. The cutoff for acceptable uniformity (LSL, lower specification limit) can be set in one embodiment as 85%, although other LSL are also contemplated.

TABLE 1

Exemplary performance of sets of primers selected for multiplex PCR.

|  | Specificity | Uniformity |
| --- | --- | --- |
| Design 1 | 81.61% ± 0.93% | 94.72% ± 0.31% |
| Design 2 | 81.40% ± 0.38% | 95.19% ± 0.31% |

Figure 6:
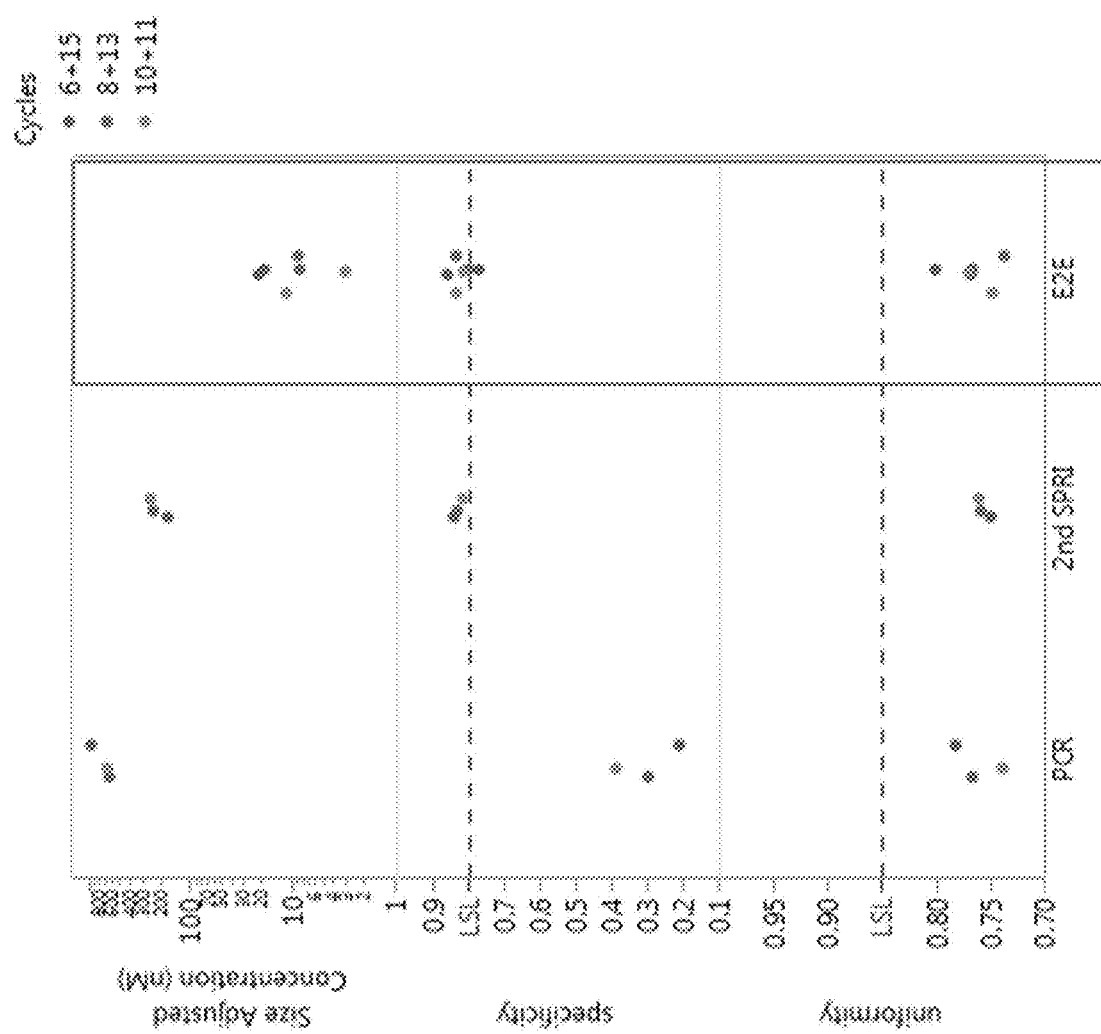
FIG. 6 shows plots of exemplary performance of sets of primers designed for multiplex PCR using a non-linear combination penalty score function.

FIG. 6 shows plots of exemplary performance of a design of 644 sets (or plexes) of primers selected using a non-linear combination penalty score function. A sample of 2 ng genomic DNA (gDNA) was amplified using the designed 644 sets of primers. In FIG. 6, "PCR" indicates the performance of multiplex PCR, "2nd SPRI" indicates the performance of multiplex PCR followed by a clean-up step using Solid Phase Reversible Immobilization (SPRI) beads, and ESE indicates multiplex PCR followed by a clean-up step using the third primers of the sets of primers.

Figure 7B:
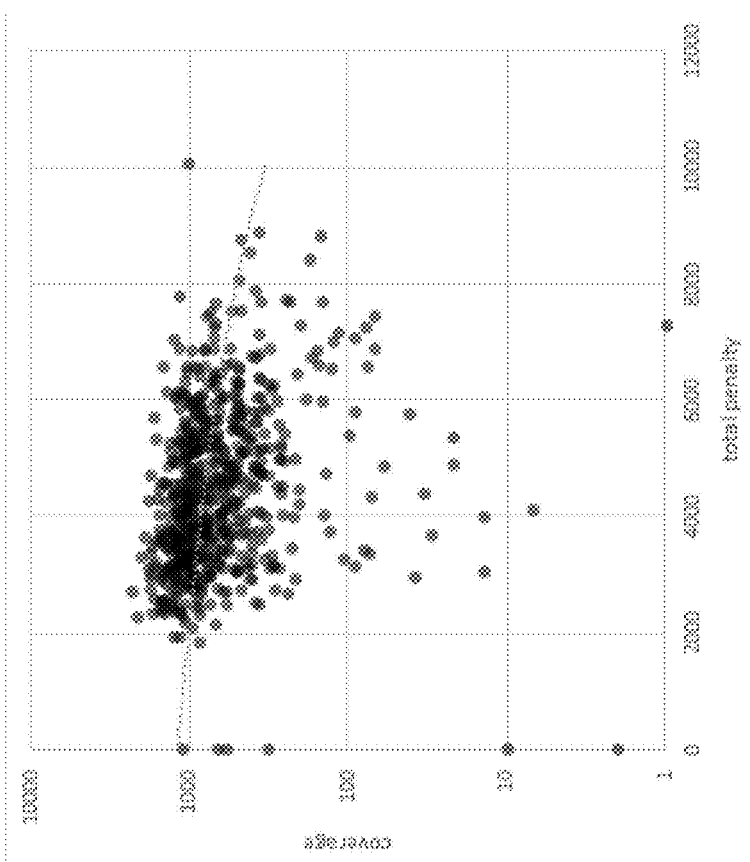
FIGS. 7A and 7B are plots showing that amplicon penalty may indicate coverage.
Figure 7A:
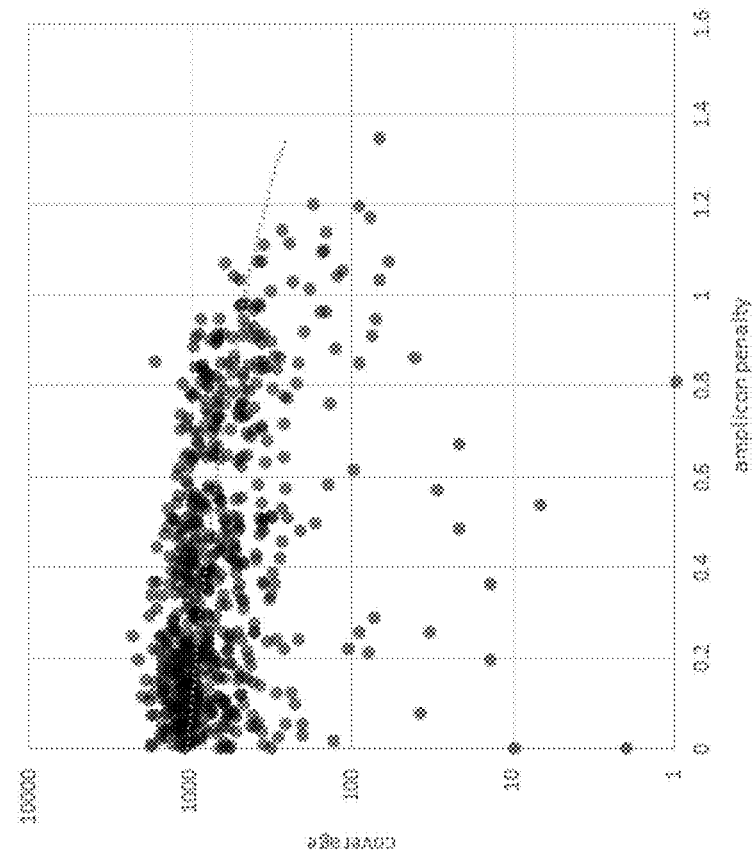

FIGS. 7A and 7B are plots showing that an amplicon penalty may indicate coverage. Overall, the amplicon penalty seems to be a good indicator of amplicon coverage, though there were a few low coverage targets found to have a low penalty. All targets with an amplicon penalty>1 had poor performance. Total penalty did not have as clear of a trend, though there was a trend. Total penalty also includes off-target penalties and dimer penalties, which may not directly affect coverage. For example, a primer could form a bad dimer, affecting specificity, but still could perform a reasonable amplification of its intended target since there are excess of primers. If the targets with the highest penalties are examined, mostly poor performers may be removed.

BRCA1 and BRCA2 Panel Design

Figure 8:
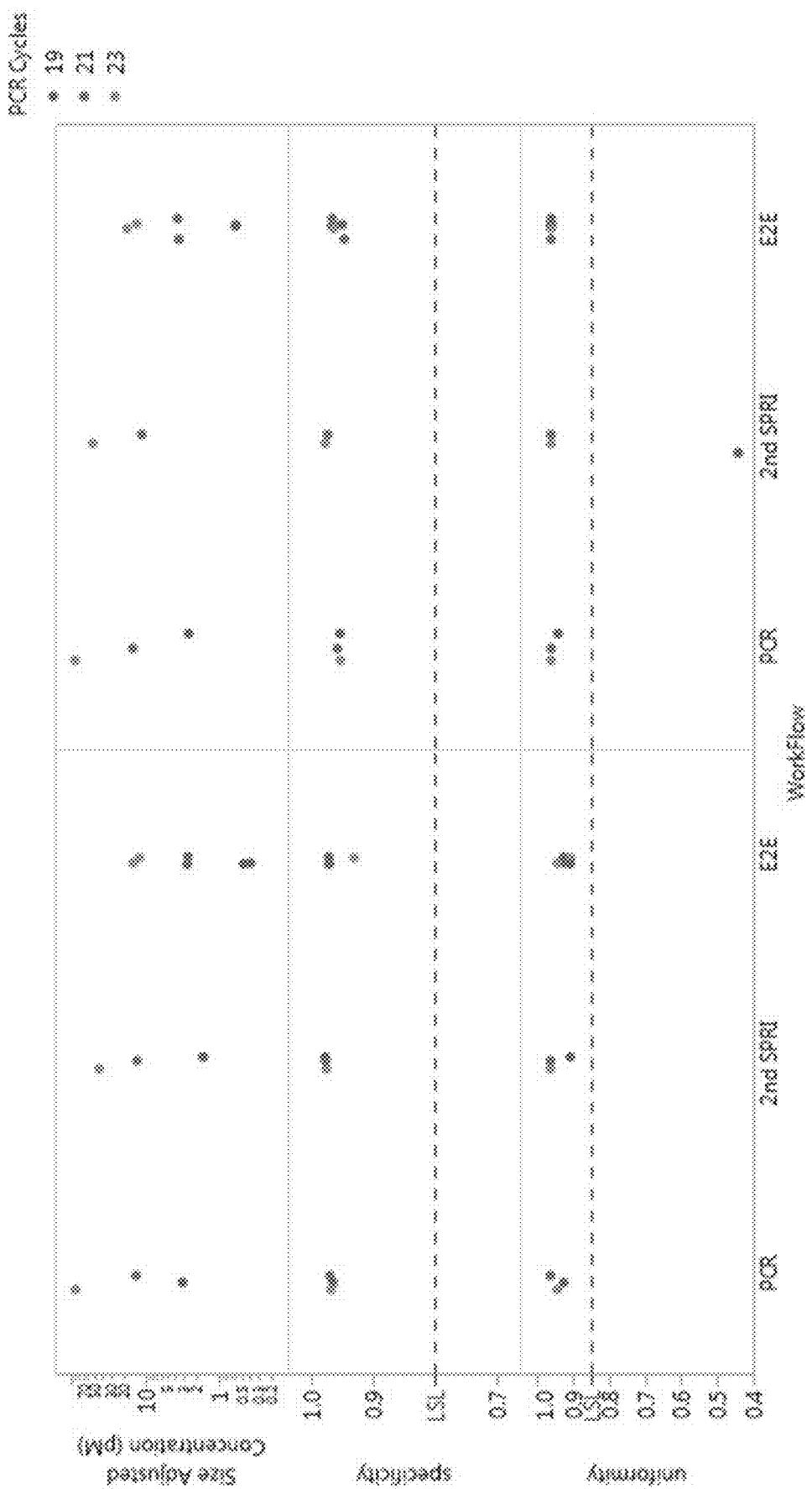
FIG. 8 shows plots of exemplary performance of sets of primers designed targeting BRCA1 and BRCA2 genes using a non-linear combination penalty score function.

This panel design was a tiling design of the exons of BRCA1 and BRCA2 in two pools of sets of primers. Tables 2 and 3 show the performance of sets of primers designed for BRCA1 and BRCA2. FIG. 8 shows plots of exemplary performance of primers designed targeting BRCA1 and BRCA2 genes using a non-linear combination penalty score function with the BRCA1 and BRCA2 exon sequences assigned to one of two pools for the design. A sample of 2 ng gDNA was subject to multiplex PCR using the two pools of 54 sets (plexes) of primers for each pool.

TABLE 2

Exemplary performance of sets of primers designed for multiplex PCR of BRCA1 and BRCA2.

| Gene | Total base pairs | Number of base pairs covered by at least one amplicon | % of base pairs covered |
|---|---|---|---|
| BRCA1 | 5658 | 5518 | 97.5256 |
| BRCA2 | 10441 | 10247 | 98.1419 |

TABLE 3

Exemplary performance of sets of primers designed for multiplex PCR of BRCA1 and BRCA2.

| Gene | Total base pairs | Cumulative number of base pairs | Number of amplicons (pool 1) | Number of amplicons (pool 2) |
|---|---|---|---|---|
| BRCA1 | 5658 | 96551 | 21 | 21 |
| BRCA2 | 10441 | 70577 | 33 | 33 |

Execution Environment

Figure 9:
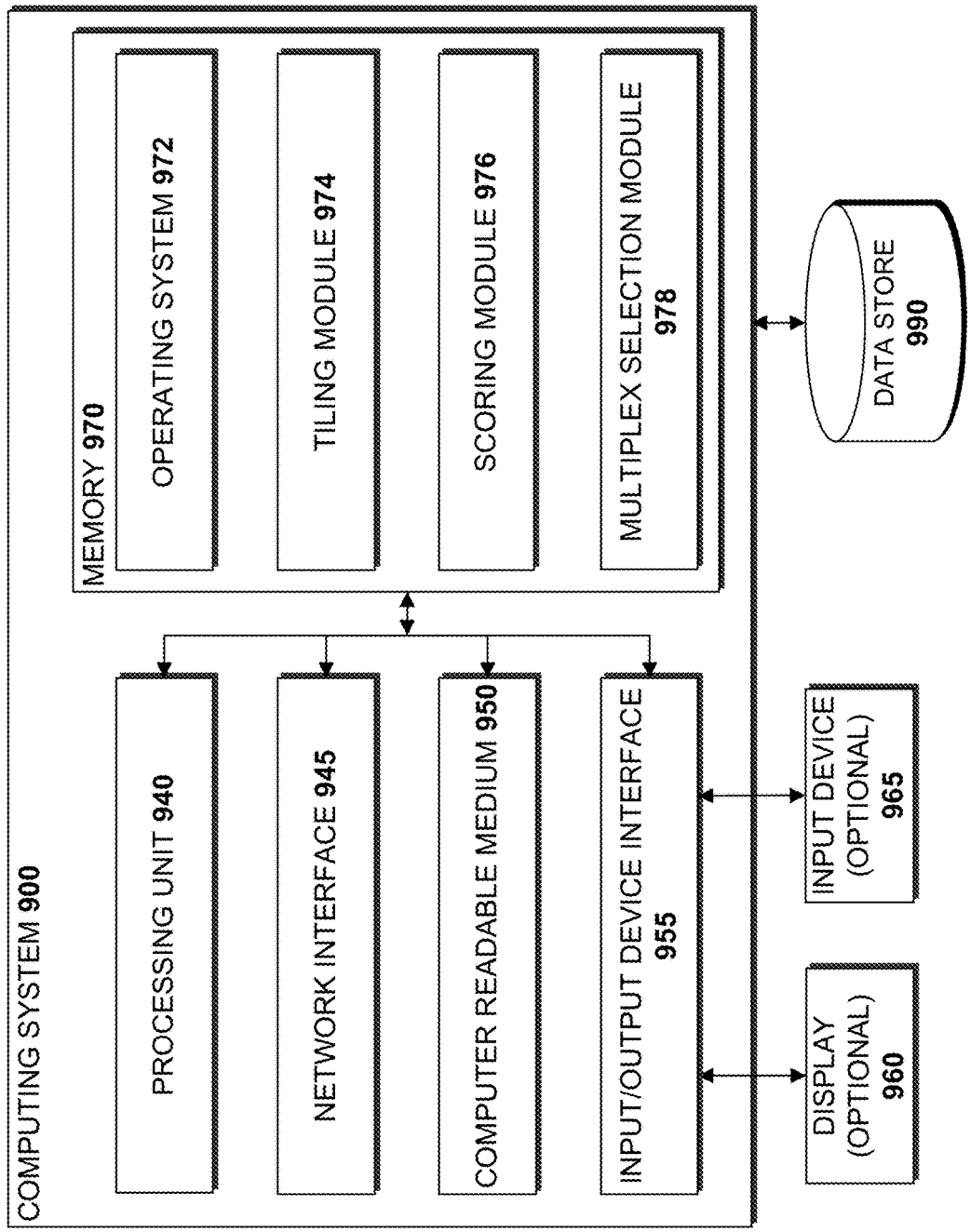
FIG. 9 is a block diagram of an illustrative computing system configured to implement the MAGI workflow.

FIG. 9 depicts a general architecture of an example computing device 900 configured to implement the metabolite, annotation and gene integration system disclosed herein. The general architecture of the computing device 900 depicted in FIG. 9 includes an arrangement of computer hardware and software components. The computing device 900 may include many more (or fewer) elements than those shown in FIG. 9. It is not necessary, however, that all of these generally conventional elements be shown in order to provide an enabling disclosure. As illustrated, the computing device 900 includes a processing unit 940, a network interface 945, a computer readable medium drive 950, an input/output device interface 955, a display 960, and an input device 965, all of which may communicate with one another by way of a communication bus. The network interface 945 may provide connectivity to one or more networks or computing systems. The processing unit 940 may thus receive information and instructions from other computing systems or services via a network. The processing unit 940 may also communicate to and from memory 970 and further provide output information for an optional display 960 via the input/output device interface 955. The input/output device interface 955 may also accept input from the optional input device 965, such as a keyboard, mouse, digital pen, microphone, touch screen, gesture recognition system, voice recognition system, gamepad, accelerometer, gyroscope, or other input device.

The memory 970 may contain computer program instructions (grouped as modules or components in some embodiments) that the processing unit 940 executes in order to implement one or more embodiments. The memory 970 generally includes RAM, ROM and/or other persistent, auxiliary or non-transitory computer-readable media. The memory 970 may store an operating system 972 that provides computer program instructions for use by the processing unit 940 in the general administration and operation of the computing device 900. The memory 970 may further include computer program instructions and other information for implementing aspects of the present disclosure.

For example, in one embodiment, the memory 970 includes a tiling module 974 for splitting each target gene sequence into sub-target regions. The memory 970 may additionally or alternatively include a scoring module 976 that determines the penalty scores for the primers selected. The memory 970 may additionally or alternatively include a multiplex selection module 978 that performs primer design, selection, and determination for multiplex PCR. In addition, memory 970 may include or communicate with the data store 990 and/or one or more other data stores that store data for and results of multiplex primer selection.

Terminology

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g.,"a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for selecting primers for amplifying sub-target regions of target gene sequences, comprising:
non-transitory memory configured to store executable instructions; and
a hardware processor programmed by the executable instructions to perform a method comprising:
receiving a plurality of target gene sequences;
determining a designability score of each target gene sequence;
splitting each target gene sequence into a plurality of sub-target regions based on the determined designability score;
assigning each sub-target region to a pool of one or more pools of sub-target regions; and
for each pool of the one or more pools:
computing a penalty score for each pair of primers in a set of candidate primer pairs per sub-target region based on a non-linear combination of properties of each candidate primer pair and properties of an amplicon amplifiable from the sub-target region using the primer pair;
computing a primer pool score between candidate primer pairs across sub-target regions within the pool; and
selecting a set of primers from the candidate primer pairs for each sub-target region in the pool based on the computed penalty scores.

2. The system of claim 1, wherein at least one pair of primers in the set of candidate primer pairs is associated with a third primer.

3. The system of claim 2, wherein the at least one pair of primers and the associated third primer comprises a forward primer, a reverse primer, and an internal primer.

4. The system of claim 3, wherein the internal primer is configured to enrich an amplicon amplifiable from a sub-target region using the forward primer and the reverse primer.

5. The system of claim 1, wherein the designability score of the target gene sequence comprises a designability score of each position of the target gene sequence.

6. The system of claim 1, wherein the designability score of the target gene sequence comprises a designability score of each sub-target region of the target gene sequence.

7. The system of claim 6, wherein the designability score of at least one sub-target region is lower than a designability score threshold.

8. The system of claim 6, wherein the designability score of each sub-target region is determined based on a number of candidate primers in the sub-target region, a quality score of the candidate primers in the sub-target region, or a combination thereof.

9. The system of claim 6, wherein the designability score of each sub-target region is determined based on a GC content of the sub-target region, presence of a poly-N stretch in the sub-target region, presence of repeats in the sub-target region, presence of a known variant in the sub-target region, or a combination thereof.

10. The system of claim 9, wherein the known variant comprises a single nucleotide polymorphism (SNP).

11. The system of claim 1, wherein the target gene sequence is split into two sub-target regions based on a minimum allowed sub-target region length, a maximum allowed sub-target region length, a length of the target gene sequence, or a combination thereof.

12. The system of claim 1, wherein the target gene sequence is split into two sub-target regions by:
determining a plurality of legal split points; and
selecting one of the plurality of legal split points as the split point for splitting the target gene sequence based on goodness scores of the resulting split.

13. The system of claim 1, wherein the one or more pools comprise a first pool and a second pool, wherein assigning each sub-target region to the pool comprises assigning each sub-target region to the first pool or the second pool.

14. The system of claim 13, wherein each sub-target region is assigned to the first pool or the second pool by balancing the number of amplicons of each target gene sequence in each pool.

15. The system of claim 13, wherein each sub-target region is assigned to the first pool or the second pool by balancing a distribution of lengths of sub-target regions in each pool.

16. The system of claim 13, wherein selecting the set of primers for each sub-target region in the pool based on the computed penalty scores comprises:
determining a first set of primers for each sub-target region in the first pool; and
determining a second set of primers in the set of candidate primer pairs for each sub-target region in the second pool independent of the first set of primers for each sub-target region in the first pool determined.

17. The system of claim 13, wherein selecting the set of primers from the candidate primer pairs for each sub-target region in the pool based on the computed penalty scores comprises:
determining first sets of primers for sub-target regions of a first target gene sequence of the plurality of target gene sequences in the first pool based on a first penalty score; and
determining second sets of primers for sub-target regions of a second target gene sequence of the plurality of target gene sequences in the first pool based on a second penalty score and the first sets of primers.

18. The system of claim 17, wherein selecting the set of primers for each sub-target region in the pool based on the computed penalty scores further comprises:
determining updated first sets of primers for sub-target regions of the first target gene sequence based on a first updated penalty score and the second sets of primers.

19. The system of claim 1, wherein the penalty score comprises an off-target penalty of the set of primers based on the specificity of the set of primers for each sub-target region in each pool relative to a reference sequence.

20. The system of claim 19, wherein the reference sequence comprises a whole human genome reference sequence, a transcriptome reference sequence, a bacterial genome reference sequence, a viral genome reference sequence, or a combination thereof.

21. The system of claim 1, wherein the hardware processor is further programmed by the executable instructions to cause synthesis of the set of primers for each sub-target region determined.

22. A computer-implemented method for determining primers for amplifying sub-target regions of target gene sequences, comprising:
receiving a plurality of target gene sequences;
computing a penalty score for each set of candidate primer per sub-target region based on a non-linear combination of properties of each candidate primer and properties of an amplicon amplifiable from the sub-target region using the candidate primers;

computing a primer pool score between candidate primers across sub-target regions; and determining a set of primers for each target gene sequence based on the computed penalties.

23. The method of claim 22, wherein the penalty score comprises a primer-level penalty score comprising thermodynamics penalty of primers in the set of primers, an adapter binding penalty, a known variant penalty, or a combination thereof.

24. The method of claim 22, wherein the penalty score comprises a set-level penalty score comprising a PCR amplicon penalty, an off-target penalty, an intra-set primer interaction penalty, or any combination thereof.

25. The method of claim 22, further comprising determining coefficients for the non-linear combination.

26. The method of claim 22, wherein determining the set of primers for each target gene sequence comprises:
ranking the set of primers for each target gene sequence based on a penalty score for the sets of primers;
iteratively determining an optimized set of primers for each target gene sequence from the set of primers with the highest penalty score to the set of primers with the lowest penalty score.

27. The method of claim 22, wherein determining the set of primers for each target gene sequence comprises:
determining first sets of optimized primers for a first target gene sequence of the plurality of target gene sequences from first sets of candidate primers based on a first penalty score; and
determining second sets of optimized primers for a second target gene sequence of the plurality of target gene sequences from second sets of candidate primers based on a second penalty score and the first sets of primers.

28. The method of claim 27, wherein determining the set of primers for each target gene sequence comprises:
determining updated first sets of optimized primers for the first target gene sequence from the first sets of candidate primers based on a first updated penalty score and the second sets of optimized primers.

29. The method of claim 28, wherein determining the updated first sets of optimized primers for the first target gene sequence comprises:
determining an updated first set of primers of the first sets of candidate primers, wherein the first penalty score is based on the first set of primers, and wherein the first updated penalty score is based on the updated first set of primers;
replacing a first set of primers of the first sets of optimized primers with the updated first set of primers of the first sets of candidate primers to generate the updated first sets of optimized primers.

30. The method of claim 29, wherein the first penalty score is at least 5% higher than the first updated penalty score.

31. The method of claim 29, wherein the first penalty score higher than the second penalty score.

32. The method of claim 29, wherein determining the set of primers for each target gene sequence comprises determining updated second sets of optimized primers for the second target gene sequence from the second sets of candidate primers based on a second updated penalty score and the updated first sets of optimized primers, wherein a first interaction penalty between the first set of primers and the second sets of optimized primers is lower than an updated first interaction penalty between the updated first set of primers and the second sets of optimized primers.

33. The method of claim 28, wherein the number of the first sets of candidate primers is greater than the number of the second sets of candidate primers.

34. The method of claim 27, wherein determining the first sets of optimized primers for the first target gene sequence comprises:
iteratively replacing a first set of primers with an updated first set of primers of the first sets of candidate primers to obtain an updated first sets of primers with a lower first penalty score.

35. The method of claim 27, wherein determining the first sets of optimized primers for the first target gene sequence comprises:
iteratively replacing a first set of primers with an updated first set of primers of the first sets of candidate primers to obtain the first sets of optimized primers with a lowest first penalty score.

36. The method of claim 22, further comprising splitting each target gene sequence of the plurality of target gene sequences into a plurality of sub-target sequences, wherein determining the set of primers for each target gene sequence comprises determining a set of primers for each sub-target sequence of the plurality of sub-target sequences.

37. The method of claim 22, further comprising causing synthesis of the set of primers that were determined.

* * * * *

SEQUENCE LISTING

<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 1
tcctcatgta ttggtctctc atgg                                          24

<210> SEQ ID NO 2
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 2
agagcatgag aggccatag                                                19

<210> SEQ ID NO 3
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 3
ctatggcctc tcatgctct                                                19

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 4
tctgaactgc agcatttact gc                                            22

<210> SEQ ID NO 5
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 5
tttctgcagc atttctttc cattg                                          25